US011071760B2

(12) United States Patent
Vallejo Galland et al.

(10) Patent No.: US 11,071,760 B2
(45) Date of Patent: Jul. 27, 2021

(54) COMPOSITIONS AND METHODS OF USE OF NOVEL STRAINS OF *LACTOBACILLUS FERMENTUM*

(71) Applicant: Dairy A Day Inc., Addison, TX (US)

(72) Inventors: Belinda Vallejo Galland, Hermosillo (MX); Aarón Fernando González Córdova, Hermosillo (MX); José Antonio Feregrino Quezada, Aguascalientes (MX); Juan Carlos Feregrino Quezada, Aguascalientes (MX)

(73) Assignee: Dairy A Day Inc., Addison, TX (US)

( * ) Notice: Subject to any disclaimer, the term of this patent is extended or adjusted under 35 U.S.C. 154(b) by 320 days.

(21) Appl. No.: 15/390,108

(22) Filed: Dec. 23, 2016

(65) Prior Publication Data
US 2017/0182101 A1    Jun. 29, 2017

Related U.S. Application Data (60) Provisional application No. 62/387,474, filed on Dec. 24, 2015.

(51) Int. Cl.
*A61K 35/747*    (2015.01)
*A23L 33/135*    (2016.01)
*A61K 9/00*    (2006.01)
*A61K 35/00*    (2006.01)
*A23C 9/123*    (2006.01)

(52) U.S. Cl.
CPC .......... *A61K 35/747* (2013.01); *A23C 9/1234* (2013.01); *A23L 33/135* (2016.08); *A61K 9/0031* (2013.01); *A61K 9/0053* (2013.01); *A61K 9/0056* (2013.01); *A61K 9/0095* (2013.01); *A23V 2002/00* (2013.01); *A23Y 2220/35* (2013.01); *A61K 2035/115* (2013.01); *A61K 2121/00* (2013.01)

(58) Field of Classification Search
None
See application file for complete search history.

(56) References Cited

U.S. PATENT DOCUMENTS

| 6,066,343 | A | 5/2000 | Megeed et al. |
| 8,349,316 | B2 | 1/2013 | Hsieh et al. |
| 2010/0266549 | A1 | 10/2010 | Zink et al. |
| 2010/0266550 | A1* | 10/2010 | Martin Jimenez ... A23C 9/1234 424/93.4 |
| 2011/0262372 | A1 | 10/2011 | Hsieh et al. |
| 2015/0190435 | A1 | 7/2015 | Henn et al. |

FOREIGN PATENT DOCUMENTS

| JP | 2012-210165 A | 11/2012 |
| WO | WO-2004087891 A1 | 10/2004 |

OTHER PUBLICATIONS

Alting et al. "Selective hydrolysis of milk proteins to facilitate the elimination of the ABBOS epitope of bovine serum albumin and other immunoreactive epitopes." Journal of Food Protection 61.8 (1998): 1007-1012 (Year: 1998).*
Church FC et al., (1983), 'Spectrophotometric Assay Using o-Phthaldialdehyde for Determination of Proteolysis in Milk and Isolated Milk Proteins,' J Dairy Sci, 66(6):1219-27.
Collado MC et al., (2008), 'Adhesion and Aggregation Properties of Probiotic and Pathogen Strains,' Eur Food Res Technol, 226(5):1065-73.
Courvalin P, (2006), 'Antibiotic Resistance: The Pros and Cons of Probiotics,' Dig Liver Dis, 38(Suppl):S261-5.
Granier A et al., (2013), 'Fermentation Products: Immunological Effects on Human and Animal Models,' Pediatr Res, 74(2):238-44.
Henikoff S and Henikoff JG, (1992), 'Amino Acid Substitution Matrices from Protein Blocks,' Proc Natl Acad Sci USA, 89(22):10915-9.
International Search Report for International Application No. PCT/US16/68557, dated May 5, 2017 (5 pages).
Maragkoudakis PA et al., (2006), 'Probiotic Potential of *Lactobacillus* Strains Isolated from Dairy Products,' Int Dairy J, 16(3):189-99.
Marin ML et al., (1997), 'Lactic Acid Bacteria: Hydrophobicity and Strength of Attachment to Meat Surfaces,' Lett Appl Microbiol, 24(1):14-8.
Mills S et al., (2011), 'Milk Intelligence: Mining Milk for Bioactive Substances Associated with Human Health,' Int Dairy J, 21(6):377-401.
Taverniti V and Guglielmetti S, (2011), 'The Immunomodulatory Properties of Probiotic Microorganisms Beyond Their Viability (Ghost Probiotics: Proposal of Paraprobiotic Concept),' Genes Nutr, 6(3):261-74.
Thirabunyanon M et al., (2009), 'Probiotic Potential of Lactic Acid Bacteria Isolated from Fermented Dairy Milks on Antiproliferation of Colon Cancer Cells,' Biotechnol Lett, 31(4):571-6.
Written Opinion of the International Searching Authority for International Application No. PCT/US16/68557, dated May 5, 2017 (9 pages).
*Lactobacillus fermentum* 16S rRNA sequence, SEQ ID 1008., Geneseq, (Aug. 27, 2015), Database accession No. BCB76625, URL: EBI, XP002790917.
LB-F strain 16S ribosomal DNA sequence, seq id 1., Geneseq, (Dec. 30, 2004), Database accession No. ADS91486, URL: EBI, XP002790933.
Biotechnology (2011), vol. 89, pp. 744-747.

(Continued)

*Primary Examiner* — Emily A Cordas
(74) *Attorney, Agent, or Firm* — Goodwin Procter LLP (57) ABSTRACT Provided herein are novel *Lactobacillus fermentum* strains, NRRL B-67059 or NRRL B-67060, compositions containing the NRRL B-67059 or NRRL B-67060 strains, and fermented dairy products and bioactive compounds prepared using the NRRL B-67059 or NRRL B-67060 strains. Also provided are methods of modulating the immune system of a subject.

17 Claims, 6 Drawing Sheets

Specification includes a Sequence Listing.

(56) References Cited

OTHER PUBLICATIONS

Kobayashi et al. (2013), PCR-Based Denaturing Gradient Gel Electrophoresis and Identification of the Microbial Consortium Present in Kimchi Treated with High Pressure, Nippon Shokuhin Kagaku Kogaku Kaishi 60(12):694-704.

* cited by examiner

SEQUENCE LISTING

<160> NUMBER OF SEQ ID NOS: 2

<210> SEQ ID NO 1
<211> LENGTH: 521
<212> TYPE: DNA
<213> ORGANISM: Lactobacillus fermentum

<400> SEQUENCE: 1

```
ggatgaacgc cggcggtgtg cctaatacat gcaagtcgaa cgcgttggcc caattgattg      60
atggtgcttg cacctgattg attttggtcg ccaacgagtg gcggacgggt gagtaacacg     120
```

```
taggtaacct gcccagaagc gggggacaac atttggaaac agatgctaat accgcataac      180
agcgttgttc gcatgaacaa cgcttaaaag atggcttctc gctatcactt ctggatggac      240
ctgcggtgca ttagcttgtt ggtggggtaa tggcctacca aggcgatgat gcatagccga      300
gttgagagac tgatcggcca caatgggact gagacacggc ccatactcct acgggaggca      360
gcagtaggga atcttccaca atgggcgcaa gcctgatgga gcaacaccgc gtgagtgaag      420
aagggtttcg gctcgtaaag ctctgttgtt aaagaagaac acgtatgaga gtaactgttc      480
atacgttgac ggtatttaac cagaaagtca cggctaacta c                          521

<210> SEQ ID NO 2
<211> LENGTH: 525
<212> TYPE: DNA
<213> ORGANISM: Lactobacillus fermentum

<400> SEQUENCE: 2
ggatgaacgc cggcggtgtg cctaatacat gcaagtcgaa cgcgttggcc caattgattg       60
atggtgcttg cacctgattg attttggttg ccaacgagtg gcggacgggt gagtaacacg      120
taggtaacct gcccagaagc gggggacaac atttggaaac agatgctaat accgcataac      180
agcgttgttc gcatgaacaa cgcttaaaag atggcttctc gctatcactt ctggatggac      240
ctgcggtgca ttagcttgtt ggtggggtaa cggcctacca aggcgatgat gcatagccga      300
gttgagagac tgatcggcca caatgggact gagacacggc ccatactcct acgggaggca      360
gcagtaggga atcttccaca atgggcgcaa gcctgatgga gcaacaccgc gtgagtgaag      420
aagggtttcg gctcgtaaag ctctgttgtt aaagaagaac acgtatgaga gtaactgttc      480
atacgtttac ggtatttaac cagaaagtca cggctaacta cgtgc                      525
```

COMPOSITIONS AND METHODS OF USE OF NOVEL STRAINS OF *LACTOBACILLUS FERMENTUM*

CROSS REFERENCE TO RELATED APPLICATIONS

This application claims the benefit of, and priority to, U.S. provisional patent application Ser. No. 62/387,474, filed Dec. 24, 2015, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Dec. 23, 2016, is named UGD-001-Sequence-Listing.txt and is 1,839 bytes in size.

BACKGROUND

Lactic acid bacteria, including those of the genera *Lactococcus*, *Lactobacillus*, *Streptococcus*, *Bifidobacterium*, and *Pediococcus*, have long been utilized as fermenting agents for the preservations of food and for preparing from milk a variety of different foodstuff such as cheese, yogurt and other fermented dairy products. More recently, some lactic acid bacteria strains have been found to exhibit beneficial properties for humans and animals including, e.g., the enhancement of immune system function.

Despite the advances made to date, there is still ongoing need for additional lactic acid bacteria strains for use in the enhancement of immune system function.

SUMMARY

This disclosure relates to new *Lactobacillus fermentum* strains, NRRL B-67059 or NRRL B-67060, and a bacterial preparation containing the same, that can produce a bioactive fermented dairy product, particularly one that modulates the immune system for better health.

In one aspect the present disclosure provides a composition or edible product including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the present disclosure provides a composition including one or more *Lactobacillus fermentum* strains that shares at least 80% to 100% sequence identity with the partial 16S rRNA gene sequence of SEQ ID NO: 1 or SEQ ID NO: 2. For example, the composition includes *Lactobacillus fermentum* strain NRRL B-67059 and/or *Lactobacillus fermentum* strain NRRL B-67060.

According to one aspect, the modulation of the immune system is the modulation of systemic IgA and the anti-inflammatory cytokine interleukin-10 (IL-10). According to another aspect, the modulation of the immune system is the modulation of the pro inflammatory cytokines interleukin-6 (IL-6) and interleukin-2 (IL-2). This biologically active fermented dairy product can be manufactured for the production of a functional food. Another aspect relates to the isolation of biologically active fractions from this fermented dairy product and their addition to a food as part of the formulation or as part of a food supplement or a pharmaceutical preparation.

*Lactobacillus fermentum* strains, NRRL B-67059 or NRRL B-67060, can be used to produce a bioactive fermented dairy product that has remarkable capacity to modulate the immune system in humans or mammals. Such bioactive fermented dairy product or its isolated biologically active fractions, provides a method for inducing, increasing or stimulating the secretion of cytokines, such as interleukin-10 (IL-10) and antibodies immunoglobulin A (IgA). On the other hand, such bioactive fermented dairy product or its active fractions did not induce a pro-inflammatory response, such as that shown by interleukin-2 (IL-2) or interleukin-6 (IL-6).

The bioactive fermented dairy product or its isolated fractions described herein is a viable option to modulate the immune system without secondary effects which are produced by some drugs. Additionally, such bioactive fermented dairy product or its isolated fractions induces anti-inflammatory effect at the systemic level. Therefore, the mentioned *Lactobacillus fermentum* strains, NRRL B-67059 or NRRL B-67060, and the bioactive compounds produced by them, may be used in pharmaceutical preparations as well as in food products.

The novel *Lactobacillus fermentum* NRRL B-67059 or NRRL B-67060 and bioactive products incorporating or derived from the novel *Lactobacillus fermentum* NRRL B-67059 or NRRL B-67060 can be administered to persons suffering from immune system deficiencies and, in particular, deficiencies in the secretion of cytokines to modulate and improve the functioning of their immune system and the secretion of cytokines.

Bioactive compounds can be generated by the action of novel *Lactobacillus fermentum* NRRL B-67059 or NRRL B-67060 during the fermentation of dairy substrates. One objective is the manufacture of food products with bioactive compounds, for the production of functional foods as a consequence of the action of specific *Lactobacillus fermentum* NRRL B-67059 or NRRL B-67060 on a substrate within the food. Also, these bioactive compounds could be used in an edible product such as a food supplement or as a pharmaceutical composition. The novel *Lactobacillus fermentum* NRRL B-67059 or NRRL B-67060 can be concentrated in manufactured food products to provide enhanced efficacy.

DETAILED DESCRIPTION

This disclosure provides, in part, novel strains of *Lactobacillus fermentum*, hereafter referred to as NRRL B-67059 and NRRL B-67060. NRRL B-67059 and NRRL B-67060 have been deposited at the National Center for Agricultural Utilization Research, United States Department of Agriculture, United States of America, on Apr. 17, 2015.

As used herein, NRRL B-67059 and NRRL B-67060 are understood to refer to the deposited strains of *Lactobacillus fermentum* as well as progeny obtained from the subculture of the isolated strains or their mutants that maintain the biological properties of the deposited NRRL B-67059 and NRRL B-67060 strains. In embodiments, *Lactobacillus fermentum* of the present disclosure shares at least 80%, 85%, 90%, 91%, 92%, 93%, 94%, 95%, 96%, 97%, 98%, or 99% genome sequence identity with the deposited NRRL B-67059 and NRRL B-67060. In embodiments, a *Lactobacillus fermentum* of the present disclosure shares at least 80%, 85%, 90%, 91%, 92%, 93%, 94%, 95%, 96%, 97%, 98%, or 99% sequence identity with the partial 16S rRNA gene sequence of SEQ ID NO: 1 or SEQ ID NO: 2, respectively.

The following abbreviations are used through the present invention:

*L. fermentum*, *Lactobacillus fermentum*; LAB, Lactic acid bacteria; cfu, colony-forming units.

Compositions

In one aspect the present disclosure provides a composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the present disclosure provides a composition including one or more *Lactobacillus fermentum* strains that shares at least 80% to 100% sequence identity with the partial 16S rRNA gene sequence of SEQ ID NO: 1 or SEQ ID NO: 2. For example, the composition includes *Lactobacillus fermentum* strain NRRL B-67059 and/or *Lactobacillus fermentum* strain NRRL B-67060. In embodiments, *Lactobacillus fermentum* strain NRRL B-67059 and/or *Lactobacillus fermentum* strain NRRL B-67060 are purified. In embodiments, the composition does or may include a bioactive agent, an additive, an excipient, an emulsifier, a therapeutic agent, and/or a preservative.

In certain embodiments, the composition of the present disclosure is formulated as a pharmaceutical composition or an edible product. For example, the pharmaceutical composition is or may be a solid dosage form, a semisolid dosage form, or a liquid dosage form. In embodiments, the solid dosage form is or may be a tablet, a lozenge, or a capsule. In embodiments, the tablet or the capsule includes microtablets, minitablets, pellets, or granulates comprising lyophilized powder of the strain. In embodiments, the semisolid dosage form is a gel, a cream, an ointment, or a chewable lozenge. In embodiments, the liquid is or may be an emulsion or a solution.

In embodiments, the composition or the pharmaceutical composition of the present disclosure may be or is formulated for oral, rectal, or parenteral administration to a subject in need thereof.

In embodiments, the edible product of the present disclosure is a food product or a food supplement. The food product or a food supplement includes or may include a food delivery vehicle. The food product or food supplement includes or may include a dairy product.

In embodiments, the edible product of the present disclosure is a dairy product.

In embodiments, the edible product of the present disclosure is a beverage.

Edible Products

In one aspect, the present disclosure provides an edible product or a pharmaceutical composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. For example, the edible product and/or the pharmaceutical composition includes *Lactobacillus fermentum* strain NRRL B-67059 and/or *Lactobacillus fermentum* strain NRRL B-67060. In embodiments, the present disclosure provides an edible product and/or a pharmaceutical composition including one or more *Lactobacillus fermentum* strains that shares at least 80% to 100% sequence identity with the partial 16S rRNA gene sequence of SEQ ID NO: 1 or SEQ ID NO: 2. In embodiments, *Lactobacillus fermentum* strain NRRL B-67059 and/or *Lactobacillus fermentum* strain NRRL B-67060 are purified.

In embodiments, the edible product or the pharmaceutical composition of the present disclosure does or may include a bioactive agent, an additive, an excipient, an emulsifier, a therapeutic agent, and/or a preservative. In certain embodiments, the edible product is a food product or a food supplement. In certain embodiments, the food product or a food supplement includes a food delivery vehicle. In certain embodiments, the food product or food supplement includes a dairy product. In certain embodiments, the edible product is prepared as a dairy product. In certain embodiments, the edible product is prepared as a beverage.

Also provided are physiological acceptable compositions that include *Lactobacillus fermentum* strains, e.g., the deposited NRRL B-67059 and NRRL B-67060 strains, and a physiologically acceptable delivery vehicle.

As used herein, "physiologically acceptable carrier" or "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. A physiologically acceptable carrier can be administered to an individual along with the relevant active compound without causing clinically unacceptable biological effects or interacting in a deleterious manner with any of the other components of the composition in which it is contained. Physiologically acceptable carriers include buffers, solvents, dispersion media, coatings, isotonic and absorption-delaying agents, and the like, that are compatible with pharmaceutical administration. Physiologically acceptable carriers include any of the standard carriers, such as a phosphate buffered saline solution, water, emulsions (e.g., such as an oil/water or water/oil emulsions), and various types of wetting agents. The compositions also can include stabilizers and preservatives. For examples of carriers, stabilizers and adjuvants, see, e.g., Martin, Remington's Pharmaceutical Sciences, 15th Ed., Mack Publ. Co., Easton, Pa. [1975]. Physiologically acceptable carriers include buffers, solvents, dispersion media, coatings, isotonic and absorption delaying agents, and the like, that are compatible with pharmaceutical administration. The use of such media and agents for pharmaceutically active substances is known in the art.

The use of such media and/or agents for pharmaceutically active substances is known in the art. In certain embodiments the composition is administered orally and includes an enteric coating suitable for regulating the site of absorption of the encapsulated substances within the digestive system or gut. For example, an enteric coating can include an ethylacrylate-methacrylic acid copolymer. The term "vehicle" as used herein refers to a medium used to carry an active agent. Vehicles of the present invention typically comprise components such as polymers and solvents.

Also provided are fermented dairy products produced using *Lactobacillus fermentum* strains, e.g., the deposited NRRL B-67059 or NRRL B-67060 strains. As used herein, the term "fermented dairy product" refers to products which are obtained by the multiplication of lactic acid bacteria, e.g., *Lactobacillus fermentum*, in a milk base leading to a milk coagulum. The milk preparation used as raw material for the fermentation may be skimmed or non-skimmed milk, optionally concentrated or in the form of powder. Furthermore, this milk preparation may have been subjected to a thermal processing operation which is at least as efficient as pasteurization. The particular characteristics of the various fermented dairy products depend upon various factors, such as the composition of milk base, the incubation temperature, the lactic acid flora and/or non-lactic acid flora. Thus, fermented dairy products manufactured herein include, for instance, various types of regular yogurt, low fat yogurt, non-fat yogurt, kefir, ymer, buttermilk, butterfat, sour cream and sour whipped cream as well as fresh cheeses. Processes for making fermented dairy products are well known in the art. As used herein, the term "bioactive dairy product" refers to a fermented dairy product that can affect a biological function. The biological activity of a bioactive dairy product may, e.g., result from particular compounds generated by *Lactobacillus fermentum* strains during the fermentation of dairy products. Accordingly, also provided herein are isolated fractions of a bioactive dairy product, i.e., bioactive dairy product fractions, or isolated compounds of a bioactive dairy product, i.e., bioactive compounds, that possess the same biological properties as the bioactive diary product. Methods for fractionating fermented dairy products or isolating compounds from fermented dairy products are well known in the art.

Disclosed *Lactobacillus fermentum* strains, bioactive dairy products, bioactive dairy product fractions, or bioactive compounds, can be formulated into physiological acceptable compositions by combination with appropriate, physiologically acceptable carriers.

Additional components of a composition can include trehalose, methylcellulose, ethylcellulose, sodium carboxymethylcellulose, hydroxypropylmethylcellulose, sodium hyaluronate, sodium alginate, chitosan and its derivatives, polyethylene glycol, glycerin, propylene glycol, Triacetin, N,N-Dimethylacetamide, pyrrolidone, dimethyl sulfoxide, ethanol, N-(-beta-Hydroxyethyl)-lactamide, 1-Methyl-2-pyrrolidinone, triglycerides, monothioglycerol, sorbitol, lecithin, methylparaben, propylparaben, polysorbates, block copolymers of ethylene oxide and propylene oxide, di-block polymers or tri-block copolymers of polyethylene oxide and polypropylene oxide, ethoxylated emulsifiers, polyethylene glycol esters, sucrose laurate, Tocopherol-PEG-succinate, phospholipids and their derivatives, and/or other non-ionic self-emulsifying agents. Additional components of a composition can include triacetine, L-Lysine, ammonium acetate.

Disclosed *Lactobacillus fermentum* strains, bioactive dairy products, bioactive dairy product fractions, or bioactive compounds, may be formulated into preparations including, e.g., tablets, capsules, powders, granules, ointments, solutions, suppositories, injections, inhalants and aerosols and topical compositions. The formulations may be designed for administration via a number of different routes, including, e.g., oral, buccal, sublingual, rectal, parenteral, intraperitoneal, intradermal, transdermal, or intracheal administration.

In embodiments the composition is a food product. Food products of interest include a disclosed *Lactobacillus fermentum* strain in combination with a food delivery vehicle. By food delivery vehicle is meant a delivery vehicle that is a nourishing substance that is eaten, drunk, or otherwise taken into the body to sustain life, provide energy, promote growth, etc. Examples of food delivery vehicles or food products of interest include, but are not limited to: baby or infant formula, baby food (e.g., pureed food suitable for infant or toddler consumption), chips, cookies, breads, spreads, creams, yogurts, liquid drinks, chocolate containing products, candies, ice creams, cereals, coffees, pureed food products, water, fluid milk products, milk, concentrated milk, fermented milk, yogurt, sour milk, frozen yogurt, lactic acid bacteria-fermented beverages, milk powder, ice cream, cream cheeses, dry cheeses, soybean milk, fermented soybean milk, vegetable-fruit juices, juices, sports drinks, confectionery, jellies, candies, infant formulas, health foods, and/or animal feeds. In embodiments, the composition is a food supplement. A food supplement may further include, e.g., a sweetener, a stabilizer, a flavoring, an emulsifier, and/or a colorant.

In embodiments, the composition (e.g., pharmaceutical composition) and/or the edible product of the present disclosure include about 0.01 mg, about 0.05 mg, about 0.1 mg, about 1 mg, about 5 mg, 10 mg, about 15 mg, about 20 mg, about 25 mg, about 30 mg, about 35 mg, about 40 mg, about 50 mg, about 60 mg, about 70 mg, about 80 mg, about 90 mg, about 100 mg, about 150 mg, about 200 mg, or about 250 mg of one or more *Lactobacillus fermentum* strains that shares at least 80% to 100% genome sequence identity with *Lactobacillus fermentum* strain NRRL B-67059 and/or *Lactobacillus fermentum* strain NRRL B-67060.

In embodiments, the composition (e.g., pharmaceutical composition) and/or the edible product of the present disclosure include about 0.01% (w/w or w/v)) to about 50% (w/w or w/v) of a bioactive agent, an additive, an excipient, an emulsifier, a therapeutic agent, a pharmaceutically acceptable carrier, and/or a preservative.

Methods of Treatment and/or Prevention

The foregoing compositions can be used to treat or prevent various medical indications.

"Treating," includes any effect, e.g., lessening, reducing, modulating, preventing, or eliminating, that results in the improvement of the condition, disease, disorder, etc. "Treating" or "treatment" of a disease state includes: (1) inhibiting the disease state, i.e., arresting the development of the disease state or its clinical symptoms; (2) relieving the disease state, i.e., causing temporary or permanent regression of the disease state or its clinical symptoms; (3) reducing or lessening the symptoms of the disease state; or (4) preventing the disease state, e.g., causing the clinical symptoms of the disease state not to develop in a subject that may be exposed to or predisposed to the disease state, but does not yet experience or display symptoms of the disease state. As used herein, "preventing" or "prevent" describes reducing or eliminating the onset of the symptoms or complications of the disease, condition or disorder. The term "preventing," when used in relation to a condition, is art-recognized, and refers to formulation, composition and/or device which reduces the frequency of, or delays the onset of, signs and/or symptoms of a medical condition in a subject relative to a subject which does not receive the composition.

By "reduce" or other forms of the word, such as "reducing" or "reduction," is meant lowering of an event or characteristic. It is understood that this is typically in relation to some standard or expected value, in other words it is relative, but that it is not always necessary for the standard or relative value to be referred to.

Insofar as the methods of the present disclosure are directed to preventing disorders, it is understood that the term "prevent" does not require that the disease state be completely thwarted. Rather, as used herein, the term preventing refers to the ability of the skilled artisan to identify a population that is susceptible to disorders, such that administration of the compounds of the present disclosure may occur prior to onset of a disease. The term does not imply that the disease state be completely avoided.

The term "ameliorating a symptom" or other forms of the word such as "ameliorate a symptom" is used herein to mean that administration of a therapeutic agent of the present disclosure mitigates one or more symptoms of a disease or a disorder in a host and/or reduces, inhibits, or eliminates a particular symptom associated with the disease or disorder prior to and/or post-administration of the therapeutic agent.

In embodiments, a disclosed compositions, e.g., a composition including a *Lactobacillus fermentum* strain, bioactive dairy product, bioactive dairy product fraction, or bioactive compounds, can used in a method treat an immune system deficiency, e.g., a deficiency in the secretion of cytokines, e.g., IL-10, IL-6 and/or IL-2. Such a method includes administering an effective amount of a disclosed composition thereby to treat the subject.

"Effective amount" or "therapeutically effective amount" as used herein, refers to the amount of an agent that is sufficient to at least partially treat a condition when administered to a patient. The therapeutically effective amount will vary depending on the condition, the route of administration of the component, and the age, weight, etc. of the patient being treated. Accordingly, an effective amount of a specific inhibitor of composition/edible product is the amount of the composition/edible product necessary for the needed purpose in a patient. An effective amount can be administered in one or more administrations, applications or dosages and is not intended to be limited to a particular formulation or administration route.

A "patient," as described herein, refers to any animal suffering from or diagnosed for a disease or disorder, including, but not limited to, mammals, primates, and humans. In certain embodiments, the patient may be a non-human mammal such as, for example, a cat, a dog, or a horse. In a preferred embodiment, the patient is a human subject.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human. The terms "subject" and "patient" may be used interchangeably, however, in some embodiments a subject may not be diagnosed with or is suffering from a disease or disorder, though may be in need of therapy.

As used in this disclosure, the term "administering" means administration as a suppository, topical contact (e.g., a spray), parenteral, intramuscular, intralesional, intrathecal, intranasal or subcutaneous administration to a subject. Administration is by any route, including parenteral and transmucosal (e.g., buccal, sublingual, palatal, gingival, nasal, vaginal, rectal, or transdermal). Other modes of delivery include, but are not limited to, the use of liposomal formulations, intravenous infusion, transdermal patches, etc.

As used in this disclosure, "sequential administration" includes that the administration of two agents (e.g., compositions described in this disclosure) occurs separately on the same day or do not occur on a same day (e.g., occurs on consecutive days).

As used in this disclosure, "concurrent administration" includes overlapping in duration at least in part. For example, when two agents (e.g., any compositions described in this disclosure that has bioactivity) are administered concurrently, their administration occurs within a certain desired time. The agents' administration may begin and end on the same day. The administration of one agent can also precede the administration of a second agent by day(s) as long as both agents are taken on the same day at least once. Similarly, the administration of one agent can extend beyond the administration of a second agent as long as both agents are taken on the same day at least once. The compositions/agents do not have to be taken at the same time each day to include concurrent administration.

As used in this disclosure, "intermittent administration includes the administration of an agent for a period of time (which can be considered a "first period of administration"), followed by a time during which the agent is not taken or is taken at a lower maintenance dose (which can be considered "off-period") followed by a period during which the agent is administered again (which can be considered a "second period of administration"). Generally, during the second phase of administration, the dosage level of the agent will match that administered during the first period of administration but can be increased or decreased as medically necessary.

By "co-administer" it is meant that a composition described in this disclosure is administered at the same time, just prior to, or just after the administration of additional therapies. The composition of the disclosure can be administered alone or can be co-administered to the patient. Co-administration is meant to include simultaneous or sequential administration of the composition individually or in combination (more than one composition or agent). The preparations can also be combined, when desired, with other active substances (e.g. for wound healing).

In embodiments, administration of a disclosed composition stimulates secretion of interleukin-10 (IL-10) and/or immunoglobulin A (IgA) antibodies immunoglobulin. In embodiments, administration of a disclosed composition does not induce a pro-inflammatory responses, e.g., as measured by interleukin-2 (IL-2) or interleukin-6 (IL-6) levels.

In embodiments, administration of a disclosed composition, e.g., a composition including a *Lactobacillus fermentum* strain, bioactive dairy product, bioactive dairy product fraction, or bioactive compound, stimulates secretion of the anti-inflammatory cytokine IL-10. Accordingly, in embodiments, a disclosed composition is used to treat an inflammatory condition. As used herein, an inflammatory condition is a disease or condition characterized, in whole or in part, by inflammation or an inflammatory response in the patient. Inflammatory may be characterized, for example, based on the primary tissue affected, the mechanism of action underlying the condition, or the portion of the immune system that is misregulated or overactive. In certain embodiments, examples of inflammatory conditions that may be treated include inflammation of the lungs (e.g., asthma, adult respiratory distress syndrome, bronchitis, pulmonary inflammation, pulmonary fibrosis, and cystic fibrosis), joints (e.g., rheumatoid arthritis, rheumatoid spondylitis, juvenile rheumatoid arthritis, osteoarthritis, gouty arthritis and other arthritic conditions), connective tissue, eyes (e.g., uveitis (including iritis), conjunctivitis, scleritis, and keratoconjunctivitis sicca), nose, bowel (e.g., Crohn's disease, ulcerative colitis, inflammatory bowel disease, inflammatory bowel syndrome, and distal proctitis), kidney (e.g., glomerulonephritis, interstitial nephritis, lupus nephritis, nephritis secondary to Wegener's disease, acute renal failure secondary to acute nephritis, Goodpasture's syndrome, postobstructive syndrome and tubular ischemia), liver (e.g., hepatitis (arising from viral infection, autoimmune responses, drug treatments, toxins, environmental agents, or as a secondary consequence of a primary disorder), obesity, biliary atresia, primary biliary cirrhosis and primary sclerosing cholangitis), skin (e.g., psoriasis, eczema, and dermatitis, e.g., eczematous dermatitides, topic and seborrheic dermatitis, allergic or irritant contact dermatitis, eczema craquelee, photoallergic dermatitis, phototoxicdermatitis, phytophotodermatitis, radiation dermatitis, and stasis dermatitis), central nervous system (e.g., multiple sclerosis and neurodegenerative diseases such as Alzheimer's disease, Parkinson's disease or dementia associated with HIV infection), vascular system (e.g. coronary infarct damage, peripheral vascular disease, myocarditis, vasculitis, revascularization of stenosis, atherosclerosis, and vascular disease associated with Type II diabetes), endocrine system (e.g., autoimmune thyroiditis (Hashimoto's disease), Type I diabetes, inflammation in liver and adipose tissue associated with Type II diabetes, and acute and chronic inflammation of the adrenal cortex) heart, or adipose tissue. The disclosure contemplates that some inflammatory conditions involve inflammation in multiple tissues. Moreover, the disclosure contemplates that some inflammatory conditions may fall into multiple categories. In certain embodiments, the inflammatory condition is an autoimmune disease. Exemplary autoimmune diseases include, but are not limited to, rheumatoid arthritis, psoriasis (including plaque psoriasis), psoriatic arthritis, ankylosing spondylitis, ulcerative colitis, multiple sclerosis, lupus, alopecia, autoimmune pancreatitis, Celiac disease, Behcet's disease, Cushing syndrome, and Grave's disease. In certain embodiments, the inflammatory condition is a rheumatoid disorder. Exemplary rheumatoid disorders include, but are not limited to, rheumatoid arthritis, juvenile arthritis, bursitis, spondylitis, gout, scleroderma, Still's disease, and vasculitis. It is noted that certain categories of conditions overlap. For example, rheumatoid arthritis is an inflammatory rheumatoid disorder, an inflammatory joint disorder, and an autoimmune disorder.

In one aspect, the present disclosure provides a method of treating a disease or disorder, e.g., a dietary disease or disorder, an inflammatory disease or disorder, and an autoimmune disease or disorder in a subject in need thereof, the method including administering to the subject an effective amount of the composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the composition described in any of its forms as described in the present disclosure is administered to the subject for treating a disease or disorder.

In one aspect, the present disclosure provides a method of modulating the immune system and/or response in a subject in need thereof, the method including administering to the subject an effective amount of the composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the composition described in any of its forms as described in the present disclosure is administered to the subject for modulating the immune system and/or response in the subject. In embodiments, the present disclosure provides a method of modulating the immune system and/or response in a subject in need thereof, the method including administering to the subject an effective amount of a composition including one or more *Lactobacillus fermentum* strains that shares at least 80% to 100% sequence identity with the partial 16S rRNA gene sequence of SEQ ID NO: 1 or SEQ ID NO: 2.

In one aspect, the present disclosure provides a method of improving immune system in a subject in need thereof, the method including administering to the subject an effective amount of a composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the present disclosure provides a method of improving immune system in a subject in need thereof, the method including administering to the subject an effective amount of a composition including one or more *Lactobacillus fermentum* strains that shares at least 80% to 100% sequence identity with the partial 16S rRNA gene sequence of SEQ ID NO: 1 or SEQ ID NO: 2.

In one aspect, the present disclosure provides a method of treating and/or ameliorating an immunodeficiency disorder in a subject in need thereof, the method including administering to the subject an effective amount of a composition including one or more *Lactobacillus fermentum* strains that shares at least 80% to 100% sequence identity with the partial 16S rRNA gene sequence of SEQ ID NO: 1 or SEQ ID NO: 2. An immunodeficiency disorder involves malfunction of the immune system, resulting in infections that develop and recur more frequently, are more severe, and last longer than usual. Immunodeficiency disorders usually result from use of a drug or from a long-lasting serious disorder (such as cancer) but occasionally are inherited. People usually have frequent, unusual, or unusually severe or prolonged infections and may develop an autoimmune disorder or cancer. Doctors suspect immunodeficiency based on symptoms and do blood tests to identify the particular disorder. People may be given antimicrobial drugs (such as antibiotics) to prevent and treat infections. Immune globulin may be given if there are too few antibodies (immunoglobulins) or they are not functioning normally. If the disorder is severe, stem cell transplantation is sometimes done. Immunodeficiency disorders impair the immune system's ability to defend the body against foreign or abnormal cells that invade or attack it (such as bacteria, viruses, fungi, and cancer cells). As a result, unusual bacterial, viral, or fungal infections or lymphomas or other cancers may develop. Another problem is that up to 25% of people who have an immunodeficiency disorder also have an autoimmune disorder (such as immune thrombocytopenia). In an autoimmune disorder, the immune system attacks the body's own tissues. Sometimes the autoimmune disorder develops before the immunodeficiency causes any symptoms.

There are two types of immunodeficiency disorders: primary and secondary. Primary disorders are usually present at birth and are usually hereditary. They typically become evident during infancy or childhood. However, some primary immunodeficiency disorders (such as common variable immunodeficiency) are not recognized until adulthood. There are more than 100 primary immunodeficiency disorders, all of which are relatively rare. Secondary disorders generally develop later in life and often result from use of certain drugs or from another disorder, such as diabetes or human immunodeficiency virus (HIV) infection. They are more common than primary immunodeficiency disorders. Some immunodeficiency disorders shorten life span. Others persist throughout life but do not affect life span, and a few resolve with or without treatment.

In one aspect, the present disclosure provides a method of improving health in a subject in need thereof, the method including administering to the subject an effective amount of the composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the present disclosure provides a method of improving health in a subject in need thereof, the method including administering to the subject an effective amount of a composition including one or more *Lactobacillus fermentum* strains that shares at least 80% to 100% sequence identity with the partial 16S rRNA gene sequence of SEQ ID NO: 1 or SEQ ID NO: 2.

In embodiments, the composition described in any of its forms as described in the present disclosure is administered to the subject for improving health of the subject. In embodiments, the improving health of the subject is achieved by modulating the immune system of the subject.

In embodiments, the composition of the present disclosure use in the methods described herein is prepared as a dairy bioactive fraction before administering to the subject.

Methods of Preparation

In one aspect, the present disclosure provides a method of preparing a food product, a food supplement, or a pharmaceutical composition including a dairy bioactive fraction of one or more *Lactobacillus fermentum* strains that shares at least 80% to 100% genome sequence identity with *Lactobacillus fermentum* strain NRRL B-67059 and/or *Lactobacillus fermentum* strain NRRL B-67060, where in the method the bioactive fraction is obtained by a bioguided procedure and used for preparing a food product, a food supplement, or a pharmaceutical composition.

In one aspect, the present disclosure provides a process for preparing an edible product, the method including fermenting a protein-containing starting material with one or more *Lactobacillus fermentum* strains that shares at least 80% to 100% genome sequence identity with *Lactobacillus fermentum* strain NRRL B-67059 and/or *Lactobacillus fermentum* strain NRRL B-67060. In embodiments, the starting material is milk or a milk-based product. In embodiments, the process for preparing an edible product involves removing unhydrolyzed protein from milk or a milk-based starting material.

In embodiments, the process for preparing an edible product includes a starting material, which includes one or more dairy bioactive fractions. The one or more dairy bioactive fractions may have immunomodulatory activity.

In embodiments, the process for preparing an edible product includes a starting material, which includes one or more bioactive compounds. The one or more bioactive compounds may have immunomodulatory activity.

In one aspect, the present disclosure provides a method of modulating the immune system in a subject in need thereof, the method including administering to the subject an effective amount of the edible product prepared by a process disclosed herein.

In one aspect, the present disclosure provides a method of treating, preventing, and/or ameliorating inflammation in a subject in need thereof, the method including administering to the subject an effective amount of the edible product prepared by a process disclosed herein.

The edible product of the present disclosure is or may be suitable for use in the dairy industry, the beverage industry, the processed food industry, the processed meat industry, the baking industry, and/or the confectionary industry.

The edible product of the present disclosure is or may be a fermented milk product. The edible product of the present disclosure is or may be a beverage. The edible product of the present disclosure is or may be a pharmaceutical composition.

In one aspect, the present disclosure provides a method of improving immune system in a subject in need thereof, the method including administering to the subject an effective amount of a composition including one or more *Lactobacillus fermentum* strains that shares at least 80% to 100% genome sequence identity with *Lactobacillus fermentum* strain NRRL B-67059 and/or *Lactobacillus fermentum* strain NRRL B-67060.

In one aspect, the present disclosure provides a method of enhancing secretion of cytokines in a subject in need thereof including administering the subject an effective amount of the composition described in this disclosure.

In embodiments, composition for improving the immune system and/or enhancing secretion of cytokines in a subject in need thereof is or may be a food product.

In embodiments, composition for improving the immune system and/or enhancing secretion of cytokines in a subject in need thereof is or may be a pharmaceutical composition.

In the composition, the edible product, the method, and the process of the present disclosure the one or more *Lactobacillus fermentum* strains is/are concentrated to provide enhanced efficacy.

Throughout the description, where compositions are described as having, including, or comprising specific components, or where processes and methods are described as having, including, or comprising specific steps, it is contemplated that, additionally, there are compositions of the present invention that consist essentially of, or consist of, the recited components, and that there are processes and methods according to the present invention that consist essentially of, or consist of, the recited processing steps.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

The terminology used herein is for the purpose of describing particular embodiments only, and is not intended to limit the scope of the present disclosure. As used throughout this disclosure, the singular forms "a," "an," and "the" include plural reference unless the context clearly dictates otherwise. Thus, for example, a reference to "a composition" includes a plurality of such compositions, as well as a single composition, and a reference to "a therapeutic agent" is a reference to one or more therapeutic and/or pharmaceutical agents and equivalents thereof known to those skilled in the art, and so forth. All percentages and ratios used herein, unless otherwise indicated, are by weight.

Unless otherwise defined, all technical and scientific terms used herein have the same meaning as commonly understood by one of ordinary skill in the art to which this disclosure belongs. In the case of conflict, the present specification will control. In the specification, the singular forms also include the plural unless the context clearly dictates otherwise. Although methods and materials similar or equivalent to those described herein can be used in the practice or testing of the present disclosure, suitable methods and materials are described below. All publications, patent applications, patents and other references mentioned herein are incorporated by reference. The references cited herein are not admitted to be prior art to the claimed disclosure. In the case of conflict, the present specification, including definitions, will control. In addition, the materials, methods and examples are illustrative only and are not intended to be limiting.

A weight percent of a component, unless specifically stated to the contrary, is based on the total weight of the formulation or composition in which the component is included.

The term "about" refers to any minimal alteration in the concentration or amount of an agent that does not change the efficacy of the agent in preparation of a formulation and in treatment of a disease or disorder. The term "about" with respect to concentration range of the agents (e.g., therapeutic/active agents) of the current disclosure also refers to any variation of a stated amount or range which would be an effective amount or range. In embodiments, the term "about" may include ±15% of a specified numerical value or data point. Ranges can be expressed in this disclosure as from "about" one particular value, and/or to "about" another particular value. When such a range is expressed, another aspect includes from the one particular value and/or to the other particular value. Similarly, when values are expressed as approximations, by use of the antecedent "about," it is understood that the particular value forms another aspect.

It is further understood that the endpoints of each of the ranges are significant both in relation to the other endpoint, and independently of the other endpoint. It is also understood that there are a number of values disclosed in this disclosure, and that each value is also disclosed as "about" that particular value in addition to the value itself. It is also understood that throughout the application, data are provided in a number of different formats and that this data represent endpoints and starting points and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

Sequence identity may be determined in various ways that are within the skill in the art, e.g., using publicly available computer software such as BLAST, BLAST-2, ALIGN or Megalign (DNASTAR) software. BLAST (Basic Local Alignment Search Tool) analysis using the algorithm employed by the programs blastp, blastn, blastx, tblastn and tblastx (Karlin et al., (1990) Proc. Natl. Acad. Sci. USA 87:2264-2268; Altschul, (1993) J. Mol. Evol. 36, 290-300; Altschul et al., (1997) Nucleic Acids Res. 25:3389-3402, incorporated by reference) are tailored for sequence similarity searching. For a discussion of basic issues in searching sequence databases see Altschul et al., (1994) Nature Genetics 6:119-129, which is fully incorporated by reference. Those skilled in the art can determine appropriate parameters for measuring alignment, including any algorithms needed to achieve maximal alignment over the full length of the sequences being compared. The search parameters for histogram, descriptions, alignments, expect (i.e., the statistical significance threshold for reporting matches against database sequences), cutoff, matrix and filter are at the default settings. The default scoring matrix used by blastp, blastx, tblastn, and tblastx is the BLOSUM62 matrix (Henikoff et al., (1992) Proc. Natl. Acad. Sci. USA 89:10915-10919, fully incorporated by reference). Four blastn parameters may be adjusted as follows: Q=10 (gap creation penalty); R=10 (gap extension penalty); wink=1 (generates word hits at every wink.sup.th position along the query); and gapw=16 (sets the window width within which gapped alignments are generated). The equivalent Blastp parameter settings may be Q=9; R=2; wink=1; and gapw=32. Searches may also be conducted using the NCBI (National Center for Biotechnology Information) BLAST Advanced Option parameter (e.g.: —G, Cost to open gap [Integer]: default=5 for nucleotides/11 for proteins; —E, Cost to extend gap [Integer]: default=2 for nucleotides/1 for proteins; —q, Penalty for nucleotide mismatch [Integer]: default=−3; —r, reward for nucleotide match [Integer]: default=1; —e, expect value [Real]: default=10; —W, wordsize [Integer]: default=11 for nucleotides/28 for megablast/3 for proteins; —y, Dropoff (X) for blast extensions in bits: default=20 for blastn/7 for others; —X, X dropoff value for gapped alignment (in bits): default=15 for all programs, not applicable to blastn; and —Z, final X dropoff value for gapped alignment (in bits): 50 for blastn, 25 for others). ClustalW for pairwise protein alignments may also be used (default parameters may include, e.g., Blosum62 matrix and Gap Opening Penalty=10 and Gap Extension Penalty=0.1). A Bestfit comparison between sequences, available in the GCG package version 10.0, uses DNA parameters GAP=50 (gap creation penalty) and LEN=3 (gap extension penalty) and the equivalent settings in protein comparisons are GAP=8 and LEN=2.

EXAMPLES

The following Examples are merely illustrative and are not intended to limit the scope or content of the invention in any way.

Example 1: Identification and Characterization of *Lactobacillus fermentum* Strains NRRL B-67059 and NRRL B-67060

The relationship between diet and health is now well known to be one of the keys to preventing disease and promoting wellbeing. This is the reason why there has been major growth in the market of functional foods that are foods that provide a positive influence on human health over and above their nutritive value. Dairy products hold a major share of this market, due partly to the fact that manufacturing process of fermented dairy products involves the addition of lactic acid bacteria (LAB), many of which are known to possess probiotic properties or which themselves produce secondary metabolites with associated health-promoting effects (Mills et al., 2011, Int. Dairy J. 21:377-401). Although, the transformation of lactose into lactic acid is the most significant phenomenon associated to LAB, fermented milks also contain a wide range of potentially active components, still not comprehensively characterized. These compounds, usually present in small amounts, are thought to exhibit specific properties, mostly in the area of immunostimulation (Granier et al., 2013, Pediatric Research 74:238-244).

Whereas lactic acid production is a feature common to all LAB, the production of other compounds depends on the bacterial strains and on the conditions of the fermentation process. Additionally, some LAB have received special attention in recent decades for their use as probiotic microorganisms. Probiotics have traditionally been defined as "live microorganisms that, when being administered in appropriate dose provide health benefits to the host" (FAO/WHO 2001). Nevertheless, scientific evidence has shown that inactivated microorganisms (heat-killed) may also positively affect human health (Taverniti and Guglielmetti 2011, Genes Nutr 6:261-274).

There is still a great need for finding new effective LAB which are useful, both as starters in fermented dairy foods and for the production of bioactive compounds with immunomodulatory and anti-inflammatory activities, that could be used as a food supplement or as a pharmaceutical composition.

Specific *Lactobacillus fermentum* strains, NRRL B-67059 or NRRL B-67060, that can produce a bioactive fermented dairy product, and have remarkable capacity to modulate the immune system in humans or mammals were isolated. Such bioactive fermented dairy product or its isolated biologically active fractions, provides a method for inducing, increasing or stimulating the secretion of cytokines, such as interleukin-10 (IL-10). On the other hand, such bioactive fermented dairy product or its active fractions did not induce a pro-inflammatory response, such as that shown by interleukin-6 (IL-6).

The bioactive fermented dairy product or its isolated fractions included in this invention is a viable option to modulate the immune system without secondary effects which are produced by some drugs. Additionally, such bioactive fermented dairy product or its isolated fractions induces anti-inflammatory effect at the systemic level. Therefore, the isolated *Lactobacillus fermentum* strains, NRRL B-67059 or NRRL B-67060, disclosed herein, and the bioactive compounds produced by them, included in this disclosure may be used in pharmaceutical preparations as well as in food products.

This disclosure includes the generation of bioactive compounds by the action of novel *Lactobacillus fermentum* NRRL B-67059 or NRRL B-67060 during the fermentation of dairy substrates. One objective of the present disclosure is the manufacture of food products with bioactive compounds, for the production of functional foods as a consequence of the action of specific *Lactobacillus fermentum* NRRL B-67059 or NRRL B-67060 on a substrate within the food. Also, these bioactive compounds could be used in an edible product such as a food supplement or as a pharmaceutical composition.

Novel strains of *Lactobacillus fermentum*, hereafter referred to as NRRL B-67059 and NRRL B-67060. NRRL B-67059 and NRRL B-67060 were isolated and were then deposited at the National Center for Agricultural Utilization Research, United States Department of Agriculture, United States of America, in Apr. 17, 2015.

This invention is related to specific *Lactobacillus* strains, NRRL B-67059 or NRRL B-67060, that can produce a bioactive fermented dairy product, mainly that have remarkable capacity to modulate the immune system in humans or mammals.

These bacteria were isolated from raw milk products and were Gram positive, catalase negative and bacilli-shaped organisms. These bacteria were identified as *Lactobacillus fermentum* by partially amplifying the 16S rRNA gene and sequencing (Table 1). These strains were characterized for their probiotic potential. Thus, *L. fermentum* strains were assessed by evaluating their resistance (percentage of survival) under conditions of low pH and enzyme treatment (Maragkoudakis et al., 2006, International Dairy Journal, 16, 189-199) and tolerance to bile salts (Thirabunyanon et al., 2009, Biotechnology Letters, 31, 571-576). In general, *L. fermentum* strains showed high viability to different gastrointestinal conditions with percentage ranges of cell survival at pH 3.0, enzyme treatment and bile salts of 94-99%, 71-99% and 79-96%, respectively (Table 2).

TABLE 1

Identification of *Lactobacillus fermentum* strains by the partial sequence of gene 16S rRNA.

Figure 1:
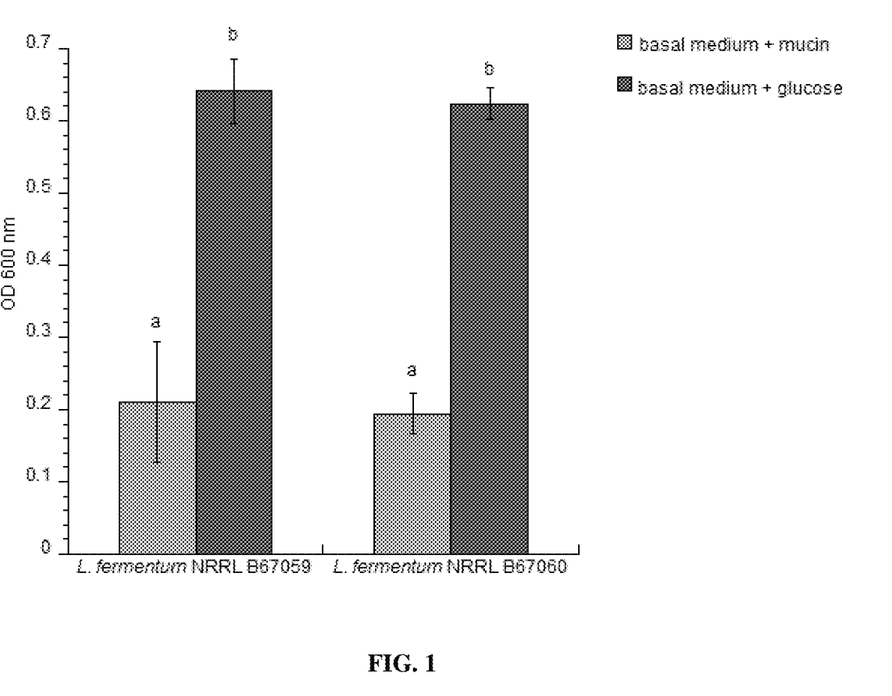
FIG. 1 is a graph showing cell growth of *Lactobacillus fermentum* NRRL B-67059 and NRRL B-67060.Optical density (0D600) was measured after incubation of cells in basal medium with mucin or glucose for 24 hours. Depicted values are means (n=3), and means for each value without a common letter differ significantly (p<0.05).

| Strain | Sequence |
|---|---|
| NRRL B-67059 | GGATGAACGCCGGCGGTGTGCCTAATACATGCAAGTCGAACGC<br>GTTGGCCCAATTGATTGATGGTGCTTGCACCTGATTGATTTTGGT<br>CGCCAACGAGTGGCGGACGGGTGAGTAACACGTAGGTAACCTG<br>CCCAGAAGCGGGGGACAACATTTGGAAACAGATGCTAATACCG<br>CATAACAGCGTTGTTCGCATGAACAACGCTTAAAAGATGGCTTC<br>TCGCTATCACTTCTGGATGGACCTGCGGTGCATTAGCTTGTTGG<br>TGGGGTAATGGCCTACCAAGGCGATGATGCATAGCCGAGTTGA<br>GAGACTGATCGGCCACAATGGGACTGAGACACGGCCCATACTC<br>CTACGGGAGGCAGCAGTAGGGAATCTTCCACAATGGGCGCAAG<br>CCTGATGGAGCAACACCGCGTGAGTGAAGAAGGGTTTCGGCTC<br>GTAAAGCTCTGTTGTTAAAGAAGAACACGTATGAGAGTAACTG<br>TTCATACGTTGACGGTATTTAACCAGAAAGTCACGGCTAACTAC<br>[SEQ ID NO: 1] |
| NRRL B-67060 | GGATGAACGCCGGCGGTGTGCCTAATACATGCAAGTCGAACGC<br>GTTGGCCCAATTGATTGATGGTGCTTGCACCTGATTGATTTTGGT<br>TGCCAACGAGTGGCGGACGGGTGAGTAACACGTAGGTAACCTG<br>CCCAGAAGCGGGGGACAACATTTGGAAACAGATGCTAATACCG<br>CATAACAGCGTTGTTCGCATGAACAACGCTTAAAAGATGGCTTC<br>TCGCTATCACTTCTGGATGGACCTGCGGTGCATTAGCTTGTTGG<br>TGGGGTAACGGCCTACCAAGGCGATGATGCATAGCCGAGTTGA<br>GAGACTGATCGGCCACAATGGGACTGAGACACGGCCCATACTC<br>CTACGGGAGGCAGCAGTAGGGAATCTTCCACAATGGGCGCAAG<br>CCTGATGGAGCAACACCGCGTGAGTGAAGAAGGGTTTCGGCTC<br>GTAAAGCTCTGTTGTTAAAGAAGAACACGTATGAGAGTAACTG<br>TTCATACGTTTACGGTATTTAACCAGAAAGTCACGGCTAACTAC<br>GTGC [SEQ ID NO: 2] | probiotics. Similarly, *L. fermentum* strains were unable to degrade mucin (FIG. 1). Mucin degradation has been regarded as a non-desirable characteristic for probiotics.

In general, antibiotic susceptibility testing (Multidisc Gram positives II, BIO-RAD) of *Lactobacillus fermentum* strains, NRRL B-67059 and NRRL B-67060, showed resistance to all antibiotics tested (Table 3). Although probiotics may be susceptible to the majority of antibiotics, their resistance can be beneficial for people with an unbalanced intestinal microbiota due to the administration of various antimicrobial agents, so that the probiotics can be administered with antibiotics to prevent the gastrointestinal side effects (Courvalin, 2006, Digestive Liver Diseases, 38, S261-S26).

Figure 2:
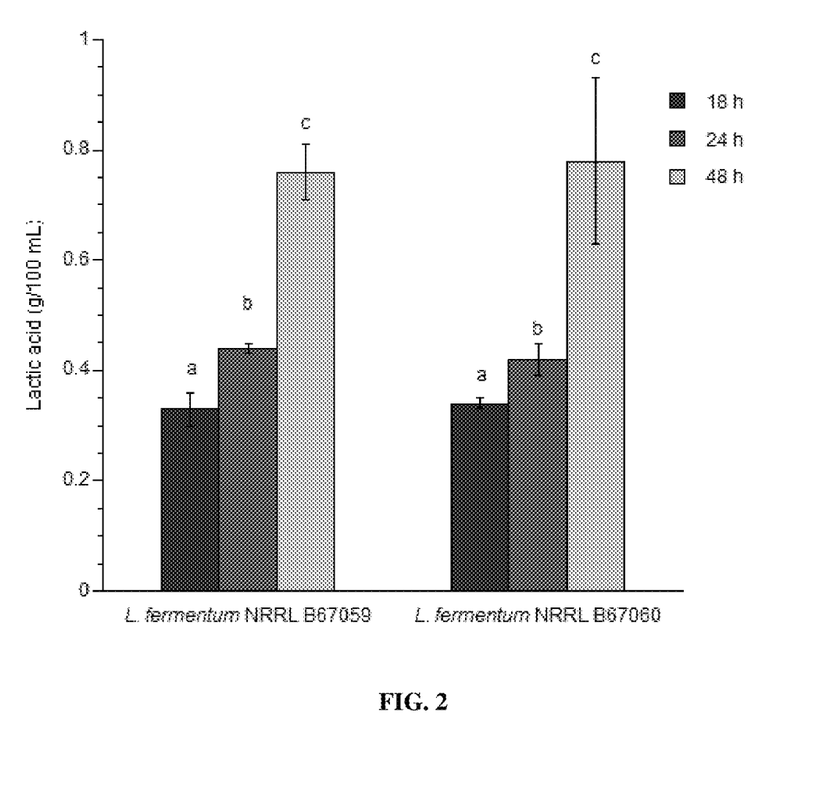
FIG. 2 is a graph showing lactic acid production in milk fermented by *Lactobacillus fermentum* NRRL B-67059 or NRRL B-67060 for the indicated time points. Depicted values are means (n=3), and means for each value without a common letter differ significantly (p<0.05).
Figure 3:
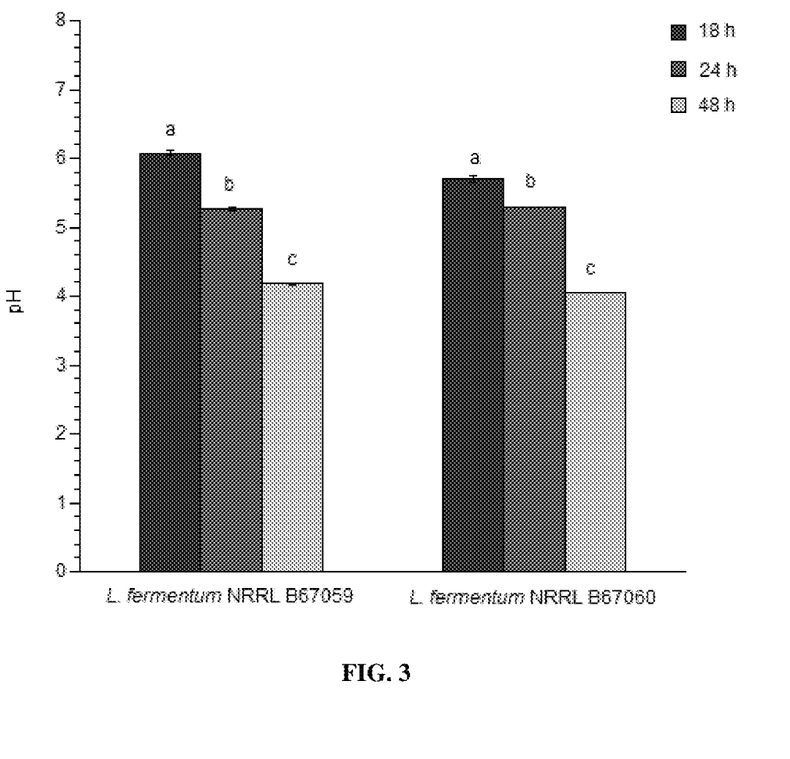
FIG. 3 is a graph showing the pH of milk fermented by *Lactobacillus fermentum* NRRL B-67059 or NRRL B-67060 for the indicated time points. Depicted values are means (n=3), and means for each value without a common letter differ significantly (p<0.05).
Figure 4:
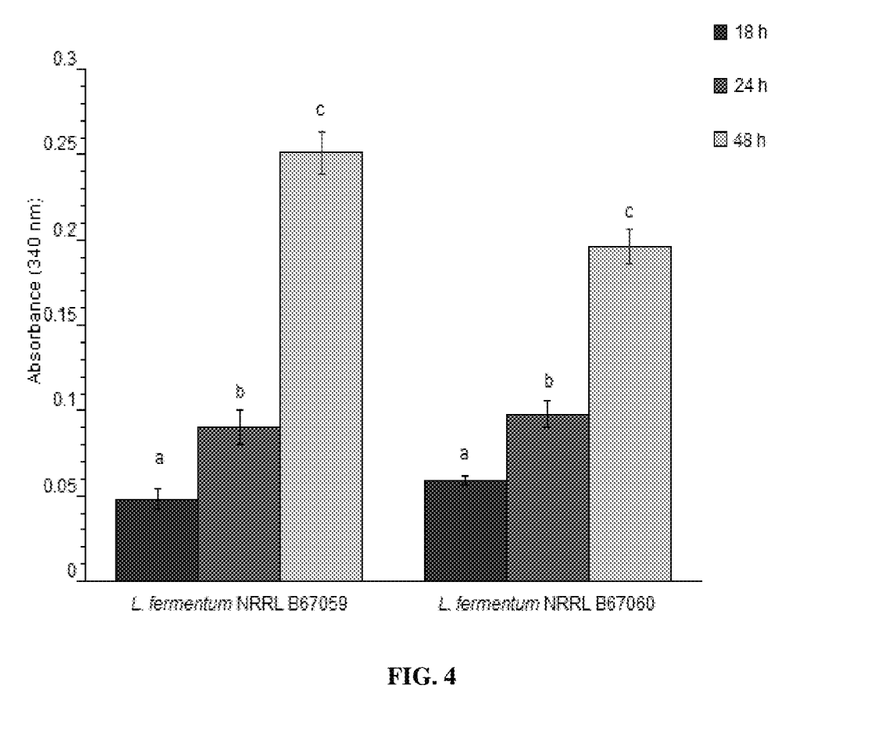
FIG. 4 is a graph showing the proteolyic activity, as measured by absorbance at 340 nm) in milk fermented by *Lactobacillus fermentum* NRRL B-67059 or NRRL B-67060 at different times of incubation. Depicted values are means (n=3), and means for each value without a common letter differ significantly (p<0.05).

Additionally, *Lactobacillus fermentum* strains, NRRL B-67059 and NRRL B-67060 presented important technological characteristics such as high acidifying and proteolytic activities when they were inoculated in reconstituted nonfat dry milk. In fact lactic acid production was significantly ($p<0.05$) higher at 48 h of fermentation for both strains (FIG. 2). Also, these strains presented high acidifying activity (pH<4.0 in 48 h) (FIG. 3) and high proteolytic activity (Abs 340>0.20 in 48h) (FIG. 4) according to the OPA (o-phtaldialdehyde method) (Church et al., 1983, J. Dairy Sci. 66:1219-1227).

TABLE 2

Characterization of *Lactobacillus fermentum* NRRL B67059 and NRRL B67060 for the evaluation of their probiotic potential.

| | | | Viability (%) | | | | |
|---|---|---|---|---|---|---|---|
| Strains | pH 3.0 | Pepsin | Pancreatin | Lysozyme | Bile salts | Autoaggregation (%) | Hydrophobicity |
| *L. fermentum* NRRL B67059 | 94.96 ± 0.31$^a$ | 96.65 ± 0.03$^a$ | 98.88 ± 0.36$^a$ | 98.73 ± 0.34$^a$ | 96.95 ± 0.10$^a$ | 31.85 ± 0.05$^a$ | 20.1 ± 1.11$^a$ |
| *L. fermentum* NRRL B67060 | 99.76 ± 0.06$^b$ | 71.56 ± 0.69$^b$ | 94.68 ± 0.15$^a$ | 99.21 ± 0.14$^a$ | 78.99 ± 0.10$^b$ | 10.57 ± 0.03$^b$ | 5.10 ± 1.59$^b$ |

Values are means for n = 3.
Means for each value without a common letter differ significantly ($p < 0.05$).

TABLE 3

*Lactobacillus fermentum* sensitivity to different antibiotics (n = 3).

| | Cephalotin | Dicloxacilin | Erythromicn | Gentamicin | Penicillin | Ampicilin | Cefepime | Cefuroxime | Tetracycline |
|---|---|---|---|---|---|---|---|---|---|
| *L. fermentum* NRRL B67059 | R | R | R | R | R | R | R | R | R |
| *L. fermentum* NRRL B67060 | R | R | R | I | R | R | R | R | R |

R = Resistant
I = Intermediate

Auto-aggregation (Collado et al. 2008, European Food Research and Technology, 226, 1065-1073) and hydrophobicity (Marín et al., 1997) were evaluated. In general, low levels of both parameters were observed (Table 2). These are properties of adhesion to epithelial cells and mucosal surfaces and may be a desirable feature for probiotics. Both strains of *L. fermentum* did not present hemolytic activity when grown on blood agar medium (Thirabunyanon, et al., 2009, Biotechnology Letters, 31, 571-576). The absence of hemolytic activity is an important property of selection for The bacterial strains *Lactobacillus fermentum* NRRL B-67059 and NRRL B-67060 were activated in MRS broth (De Man, Rogosa and Sharpe, Difco) in three consecutive sub-cultures, these were inoculated at 1% level and incubated at 37° C. for 24, 18 and 12 h, respectively. Fresh cultures were obtained by repeating the same procedure. Initial starter cultures were prepared by allowing *L. fermentum* strains to reach $10^6$-$10^7$ colony-forming units (CFU) $mL^{-1}$ as enumerated on MRS agar.

Example 2: Production of Fermented Milk Containing Bioactive Compounds

Reconstituted nonfat dry milk (10%, w/v) was sterilized at 110° C. for 10 min. The pre-culture ($10^7$ CFU mL$^{-1}$) of Lactobacillus fermentum NRRL B-67059 or NRRL B-67060 was inoculated into sterilized milk at 1% level and incubated for 12 h. Then, milk (20 mL) was inoculated with 3% of pre-culture. Samples were incubated at 37° C. for 48 h to obtain the different fermented milk batches ($10^9$ CFU mL$^{-1}$). For fermented-pasteurized milk preparation, fermented milk was subjected to 75° C. for 15 min.

Example 3: Immunomodulatory Effect After Administration of Fermented Milk with Lactobacillus fermentum Strains NRRL B-67059 or NRRL B-67060

Samples (1 mL, $10^9$ CFU mL$^{-1}$) of specific fermented milk (prepared as previously described) were administered via canula to female Wistar rats (6-8 week-old, weighing 140±20 g) obtained from Harlan Laboratories, INC, (Indianapolis, Ind., USA, through their Mexico city representative). The control groups were administered unfermented milk. Rats were randomly assigned to groups of six and housed in pairs per cage at 23±2° C. with 12 h light/dark cycles, 52±6% relative humidity, with ad libitum intake of a standard diet (Teklad, Harlan Laboratories, USA) and purified water. Blood samples were obtained from each group after 7 and 21 d of treatment administration, before animals were sacrificed. Blood samples were centrifuged (1800×g, 10 min, 4° C.) and serum samples were stored −20° C. until cytokine analysis. The animal experimental procedures were done following the guidelines and supervision of the CIAD, A.C. Committee of Ethics for scientific research.

The concentration of cytokines (IL-10 and IL-6) was evaluated by a commercial ELISA kit (BD, Invitrogen). The results were expressed as concentration of each cytokine (pg mL-1).

Figure 5:
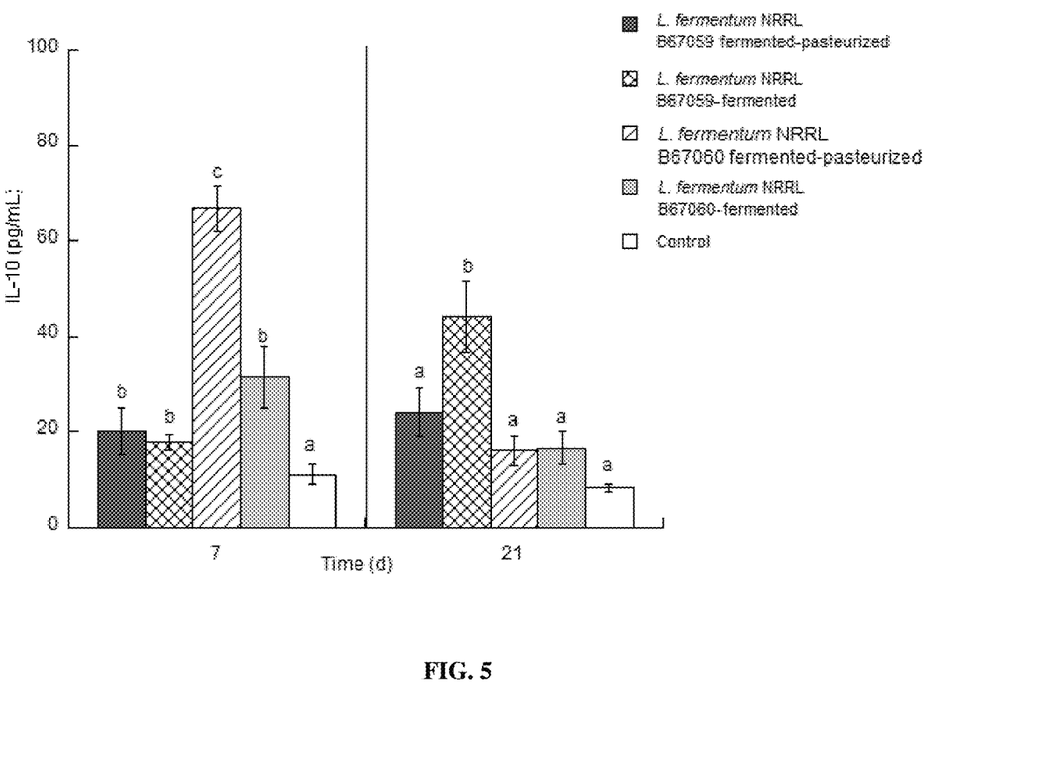
FIG. 5 is a graph showing the effect of oral administration of milk fermented with *Lactobacillus fermentum* NRRL B-67059 or NRRL B-67060 on anti-inflammatory cytokine IL-10 production in rats. Depicted values are means (n=6), and means for each value without a common letter differ significantly (p<0.05).
Figure 6:
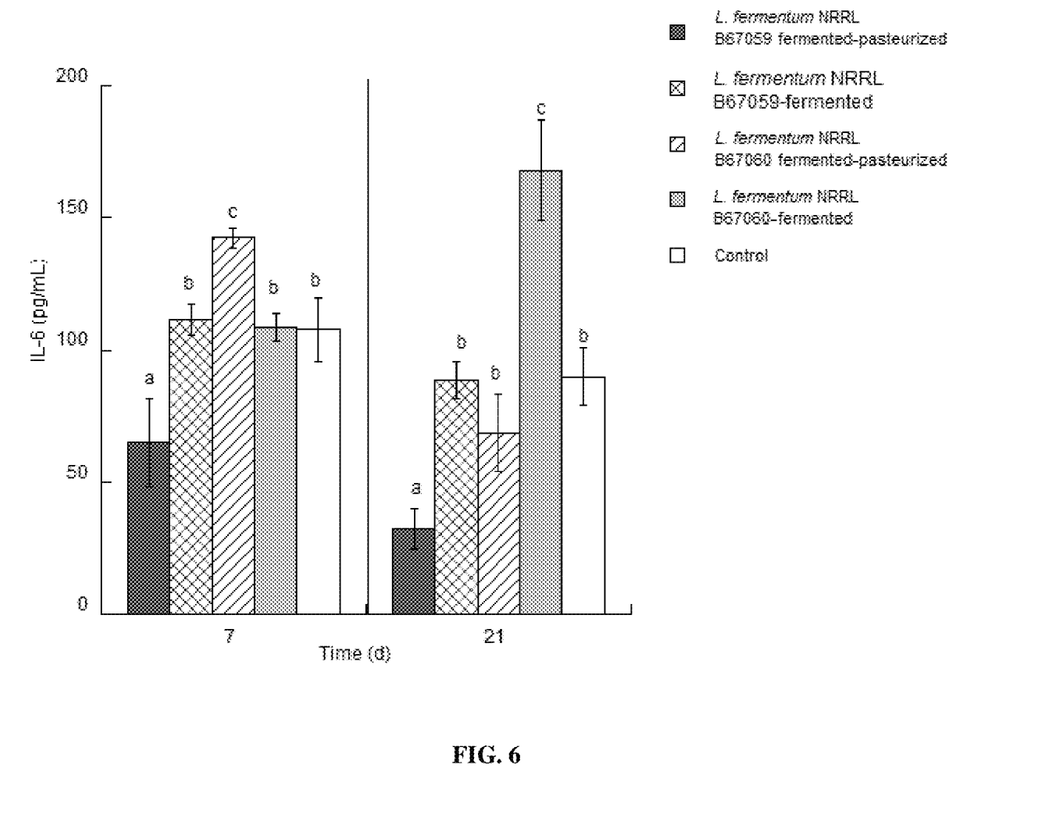
FIG. 6 is a graph showing the effect of oral administration of milk fermented with *Lactobacillus fermentum* NRRL B-67059 or NRRL B-67060 on pro-inflammatory cytokine IL-6 production in rats. Depicted values are means (n=6), and means for each value without a common letter differ significantly (p<0.05).

All groups administered with fermented milk containing Lactobacillus fermentum NRRL B-67059 or NRRL B-67060 presented significantly ($p<0.05$) higher anti-inflammatory cytokine IL-10 than the control group after 7 days of treatment (FIG. 5). Furthermore, the concentration of IL-10 was maintained at higher levels than the control at 21 d, although only treatment with milk fermented with Lactobacillus fermentum NRRL B-67059 was highly significant ($p<0.05$) (FIG. 5). Furthermore, the concentration of the pro-inflammatory cytokine IL-6 decreased significantly ($p<0.05$) in the group that consumed fermented-pasteurized milk with Lactobacillus fermentum NRRL B-67059 with respect to the control group (FIG. 6). Therefore, the beneficial effect on the immune system may be attributed to bioactive compounds produced during fermentation (postbiotics) and/or live or heat-killed bacteria.

Thus, the use of milk fermented by specific lactic acid bacteria Lactobacillus fermentum NRRL B-67059 or NRRL B-67060, may be considered as a co-adjuvant for the improvement of health by modulating the immune system. Thus, dairy products fermented with Lactobacillus fermentum NRRL B-67059 or NRRL B-67060, may be used as functional foods with potential benefits.

A method is performed for preparing a food product, a food supplement, or a pharmaceutical composition including a dairy bioactive fraction of one or more Lactobacillus fermentum strains that shares at least 80% to 100% genome sequence identity with Lactobacillus fermentum strain NRRL B-67059 and/or Lactobacillus fermentum strain NRRL B-67060, where the bioactive fraction is obtained by a bioguided procedure and used for preparing the food product, the food supplement, or the pharmaceutical composition.

A process is described for preparing an edible product, the process including fermenting a protein-containing starting material with one or more Lactobacillus fermentum strains that shares at least 80% to 100% genome sequence identity with Lactobacillus fermentum strain NRRL B-67059 and/or Lactobacillus fermentum strain NRRL B-67060. The starting material is milk or a milk-based product. The method includes removing unhydrolyzed protein. The edible product includes a bioactive fraction. In the process, the starting material may include one or more bioactive compounds.

A subject is administered with a composition, pharmaceutical composition, and/or an edible product of the present disclosure for treating a dietary disease or disorder, an inflammatory disease or disorder, and/or an immune disease or disorder.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

---

What is claimed is:

1. A composition formulated as an edible product, comprising *Lactobacillus fermentum* strain NRRL B-67059 and/or *Lactobacillus fermentum* strain NRRL B-67060, wherein the edible product is a food product or a food supplement comprising a dairy product, wherein the edible product does not comprise unhydrolyzed proteins.

2. The composition of claim 1, further comprising a bioactive agent, an additive, an emulsifier, a therapeutic agent, and/or a preservative.

3. The composition of claim 1, wherein the food product or the food supplement comprises a food delivery vehicle.

4. The composition of claim 1, wherein the food product is a dairy product.

5. The composition of claim 1, wherein the edible product is a beverage.

6. An edible product comprising *Lactobacillus fermentum* strain NRRL B-67059 and/or *Lactobacillus fermentum* strain NRRL B-67060, wherein the edible product is a food product or a food supplement comprising a fermented dairy product, wherein the fermented dairy product does not comprise unhydrolyzed proteins.

7. The edible product of claim 6, further comprising a bioactive agent, an additive, an emulsifier, a therapeutic agent, and/or a preservative.

8. The edible product of claim 6, wherein the food product or the food supplement comprises a food delivery vehicle.

9. The edible product of claim 6, prepared as a beverage.

10. A method of treating a disease or disorder selected from the group consisting of: a dietary disease or disorder, an inflammatory disease or disorder, and an autoimmune disease or disorder in a subject in need thereof, the method comprising administering to the subject an effective amount of the composition of claim 1.

11. The method of claim 10, wherein the composition is prepared as a dairy bioactive fraction before administering to the subject.

12. A method of modulating the immune system in a subject in need thereof, the method comprising administering to the subject an effective amount of the composition of claim 1.

13. A method of improving health in a subject in need thereof, the method comprising administering to the subject an effective amount of the composition of claim 1.

14. The method of claim 13, wherein the improving the health of the subject is achieved by modulating the immune system of the subject.

15. A method of improving the immune system in a subject in need thereof, the method comprising administering to the subject an effective amount of the composition of claim 1.

16. The method of claim 15, wherein the composition is a food product.

17. A method of enhancing secretion of cytokines in a subject in need thereof, the method comprising administering to the subject an effective amount of the composition of claim 1.

* * * * *